United States Patent [19]

Ohnishi et al.

[11] 4,291,981

[45] Sep. 29, 1981

[54] REFERENCE SCATTER FOR USE IN THE CORRECTION OF SCATTERING PHOTOMETERS

[75] Inventors: Masaaki Ohnishi, Settsu; Akio Saito, Kyoto, both of Japan

[73] Assignee: Kabushiki Kaisha Kyoto Daiichi Kagaku, Kyoto, Japan

[21] Appl. No.: 23,407

[22] Filed: Mar. 23, 1979

[30] Foreign Application Priority Data

Apr. 5, 1978 [JP] Japan .................................. 53-40685

[51] Int. Cl.³ .......................................... G01N 21/15
[52] U.S. Cl. ........................................ 356/244; 350/65
[58] Field of Search .................... 250/252; 350/61, 65, 350/67, 188; 356/243, 256, 230, 42, 445–448, 244

[56] References Cited

U.S. PATENT DOCUMENTS 4,202,608  5/1980  Kaufmann .......................... 356/334

FOREIGN PATENT DOCUMENTS 51-20914  6/1976  Japan ................................. 356/244

Primary Examiner—John K. Corbin
Assistant Examiner—Bruce Y. Arnold
Attorney, Agent, or Firm—Darby & Darby

[57] ABSTRACT

A reference scatterer for use in the correction of scattering type photometers having a reference glass scatterer main body with microcrystals therein to split the phase of incident light which is housed within a vessel with a clearance between the two. The clearance is filled with a liquid whose index of refraction substantially matches that of the main body.

11 Claims, 9 Drawing Figures

REFERENCE SCATTER FOR USE IN THE CORRECTION OF SCATTERING PHOTOMETERS

BACKGROUND OF THE INVENTION AND PRIOR ART STATEMENT

The present invention relates to an improvement of a reference scatterer for use in the correction of scattering photometers.

In the analysis of samples, there are utilized a variety of detection principles, of which the scattering photometric method is widely used for analyzing liquid samples as well as the absorbance photometric method. The scattering photometric method is able to detect the turbidity of liquid samples with high sensitivity, whereby various objectives of the analysis come to be achieved with the improvement of apparatus for measuring the luminous intensity of scattered light. This enables analysis with great accuracy such as, for example, the analysis of a microquantity of immune albumine contained in blood through the utilization of the antigen-antibody reaction in the clinical examination, and the analysis of the molecular weight of a macromolecule.

Nevertheless, in order to obtain the high accuracy of quantitative determination at the time of such analysis as above-mentioned, the provision of a superior kind of correcting means is required over and above the sensitivity of the instrument. In the case of the absorbance photometric method, the appropriate correction of the instrument can be made by running a sample blank and then checking the blank value against the 100%-indication of the meter. But such a procedure by a blank test is not useful for the scattering photometric method, as easily understood from its measuring principle. There is no choice in this case but either to adopt another standard for scatterers in place of the sample blank test or to conduct some analytical procedure on both an unknown sample and a sample of already-known concentration with the object of finding the analytical value of the unknown sample through the correlation between the above-mentioned two.

However, the latter procedures require a large quantity of analytical grade reagent. Accordingly, it is not only uneconomical but also at the same time it takes much time and labor because standard samples must be made each time when treating the samples resulting from the reaction, for example, such as the antigen-antibody reaction whose turbidity is liable to fluctuate with time. And what is worse, there is no guarantee of being able to obtain at all times a standard sample for the substance to be analyzed. There are frequent occasions when it is extremely difficult to procure the standard sample according to this method.

To overcome the problem in such a case, it is important to standarize the analytical process as well as the correcting means. Among others, as the standard for correcting the scattering photometer which is employed in measuring the quantity of scattered substances dispersed in solution, heretofore in general there has been used a liquid-phase reference scatterer which had aluminum oxide powder, polystyrene latex or the like dispersed in solution. However, a liquid-phase reference scatterer of this type is insufficient to correct a scattering photometer of high accuracy because its scattered particles are liable to aggregate and bond together within the solution, so that the homogeneous dispersion of particles can not be maintained for a long period of time.

Under these circumstances, there has been developed previously a reference glass scatterer. In this reference glass scatterer a small quantity of foreign matter was added to silicon oxide as the main ingredient of glass, and after both were fused together, they were annealed at proper temperature to make microcrystals as a phase splitting of borosilicic acid grown with the foreign matter as nuclei (Japanese Patent Disclosure No. 20914-1976). The grain diameter of the microcrystal depends on the temperature and time of annealing. If these conditions are fixed and observed, it becomes possible to obtain a reference glass scatterer having the desired particle size distribution. Unlike the before-described liquid-phase reference scatterer, the reference glass scatterer thus constructed had excellent the long-term stability and reproducibility and has been used so far for the correction of scattering photometers of high accuracy.

Nevertheless, the reference glass scatterer main body 1 has an uneven, or rough though fine surface. This is shown in a partially enlarged view in FIG. 1 as a result dirt and moisture easily adhere to the surface, while, on the other hand, it is hard to remove them therefrom. There is further the fear of the surface being injured in trying to wipe the dirt and moisture off while cleaning. The phenomenon of such unevenness arises from the fact that since the particles of the microcrystals 2 are harder than the glass portion 3, the latter is more readily to be cut away in the process of grinding the surface. FIG. 2 is a partially enlarged view of the surface of an ordinary glass body enlarged in the same way as in FIG. 1.

In the case where a reference glass scatterer having a flaw or dirt on its surface is used a series of phenomena occur such as the absorption, reflection or refraction of light, as a sequel to which the reference value acquired can be often wrong. On the other hand, glass is apt to absorb moisture which remains on the surface of the reference glass scatterer and has the same influence as the above-mentioned dirt. There are other points in question, for example, such as the unevenness of the surface of the glass scatterer fluctuates depending on how the grinding operation has been done. Because of this the scattering power of the thus-manufactured scattering plates are likely to vary widely.

SUMMARY OF THE INVENTION

The present invention has for its object the provision of a reference scatterer capable of functioning satisfactorily by being constructed in such manner that the reference glass scatter main body may be accomodated in a transparent vessel. The scatterer and the vessel form a dual structure, and the clearance created between the two is filled up with a suitable liquid, with the result that dirt and moisture find it difficult to adhere to the surface of the reference scatterer main body. If either dirt or moisture sticks, they can be easily wiped off without injuring the surface of the reference scatterer main body.

BRIEF DESCRIPTION OF THE DRAWINGS

FIGS. 6 to 8 show individually another example of which FIG. 6 is a longitudinal sectional view, FIG. 7 is a view of the flux of light seen from above within the reference scatter, and FIG. 8 is a typical view of the same flux of light seen from the side.

DETAILED DESCRIPTION OF A PREFERRED EMBODIMENT

Figure 1:
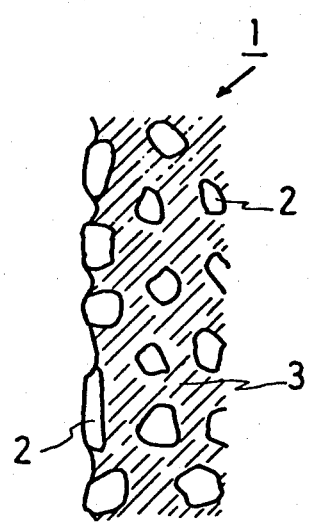
FIG. 1 is an enlarged view of part of a reference glass scatterer main body heretofor in use.
Figure 2:
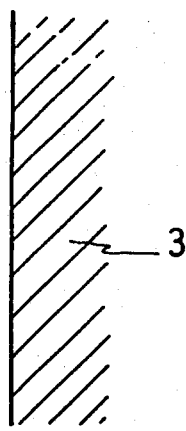
FIG. 2 is an enlarged view of part of an ordinary glass body.
Figure 3:
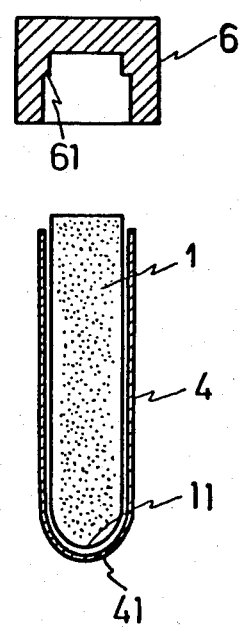
FIG. 3 is an exploded view of the reference scatterer according to the present invention.
Figure 4:
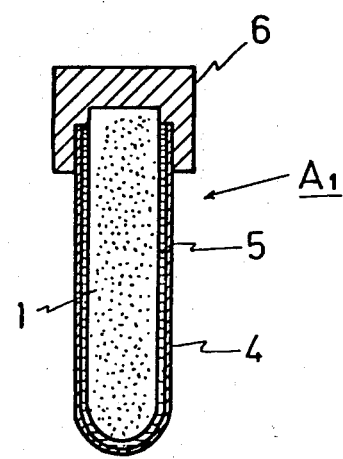
FIG. 4 is a longitudinal sectional view of the reference scatterer of FIG. 3 in the assembled form.

FIGS. 3 and 4 show an example of the reference glass scatterer according to the present invention wherein a reference glass scatterer main body 1 in the shape of a column or cylinder is accommodated, or held, in a transparent vessel 4. The clearance between the body and the vessel is filled with silicone oil 5, and after that the unit is closed by a cap 6. The reference glass scatterer main body 1 is formed with a spherical surface at its bottom to receive incident light, while the transparent vessel 4 has the shape of a cylinder which is with a spherical bottom open at its upper end. The internal diameter of the vessel is larger than the external diameter of the reference glass scatterer main body 1. The material used for the transparent vessel 4 can be of transparent synthetic resin or glass. Glass is the most desirable material from the standpoint of chemical stability, hardness, and so on.

The cap 6 is provided, on the one hand, for the purpose of preventing silicone oil filled up in the clearance from leaking or evaporating. On the other hand it has the function to connect and hold together the reference glass scatterer main body 1 and the transparent vessel 4. In order to fulfill the above two purposes, the cap 6 is formed with an annular step 61 within its cavity. In this connection, it is preferable that a somewhat black-colored cap 6 be used so as to be able to prevent better the reflection of light.

The transparent vessel 4 has the object of protecting the reference glass scatterer main body 1. At the same time it is necessary that this transparent vessel 4 be easily exchanged in case of being damaged. Therefore, it is inconvenient when both 1 and 4 are adhered to each other or integrated in one body. Accordingly, the transparent vessel 4 is usually made slightly larger size relative to the reference scatterer main body 1, so that some clearance is produced between the former and the latter. As a result, there is a chance of reflection of light between this clearance and the transparent vessel or else of unevenness of the scattered light occurring due to the roughness of the surface treatment of the reference glass scatterer main body 1. To prevent such phenomena from occurring the above-mentioned clearance is filled with a certain kind of liquid. It is required that this liquid be chemically inert and non-volatile and that the temperature dependence of its refractive index be small.

For the purpose of minimizing the unevenness of the scattered light attributable to the reflection of light and other factors, the more closely the refractive index of the liquid approximates to that of glass the better. Silicone oil is, indeed, a realtively ideal type of liquid, but the liquid to be used is not limited only to silicone oil. If bubbles are possibly contained in the liquid, the flux of light reflects or refracts to give rise to some measuring errors, so that it must be used after defoaming it.

FIG. 4 shows the assembled reference scatterer A1 into which the scatterer main body 1 and the transparent vessel 4 are assembled by holding them together with cap 6 after having poured silicone oil 5 into the clearance inbetween and then defoaming it.

Figure 5:
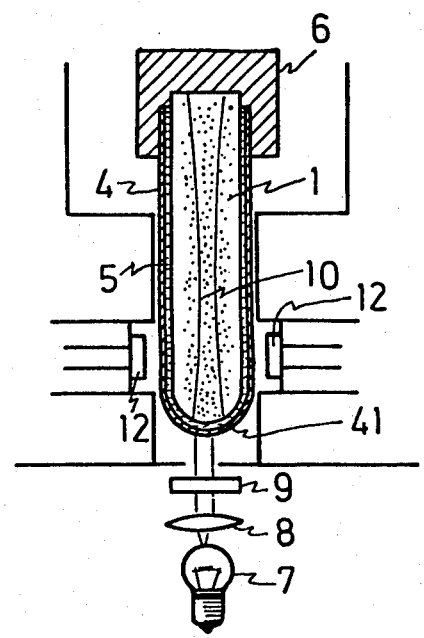
FIGS. 5 and 9 each schematic diagrams showing several states of employment of the reference scatterer.

FIG. 5 is a schematic diagram showing the use of the reference scatterer A1. Light from a light source lamp 7 reaches the bottom 41 which serves as the receiver of incident light for the transparent vessel 4, after having passed through a lens (8) and a filter (9). That bottom 41 is fabricated with a spherical surface shaped so as to condense the incident light and minimize the divengence of light, whereby the scattered light from the microcrystals is able to be obtained effectively. The flux of light condensed by the face of curved lens surface 41 of the transparent vessel enters into the layer of silicone oil. Since the refractive index of silicone oil layer approximates that of glass, the flux of light in the silicone oil layer is propagated similarly to the case of glass, so that its reflection in the interface between glass and silicone oil is negligible. The flux of light, which has passed through the silicone oil layer, arrives at the reference glass scatterer main body 1 and is scattered there by the microcrystals 2 which are dispersed in the reference glass main body. In the figure, reference numeral 10 indicates the flux of light being propagated through the reference glass scatterer main body 1. In this case, the bottom of the reference glass scatterer main body 1 is also formed with a spherical surface, so that the flux of light 10 is propagated in the shape of back-to-back arcs. Reflection from the top part is prevented by virtue of the dark cap. The scattered light dispersed by the microcrystals 2 passes through the layer of silicone oil 5 and the transparent vessel 4 and back again, and then is detected by means of the optical detector 12.

In the above-mentioned example, both the base 41 of the transparent vessel as the receiver of incident light and the bottom 11 of the reference glass scatterer main body 1 are fabricated separately with a spherical lens type, surface. This is for the purpose of condensing the incident light and doing away with the divergence of light, whereby the scattered light dispersed by the microcrystals is able to be obtained effectively. Also in the case where the base 41 as the receiver of incident light and the bottom 11 of the scatterer main body are both formed with a plane surface, a problem does not arise apart from the lack of the ability to condense the incident light.

Figure 6:
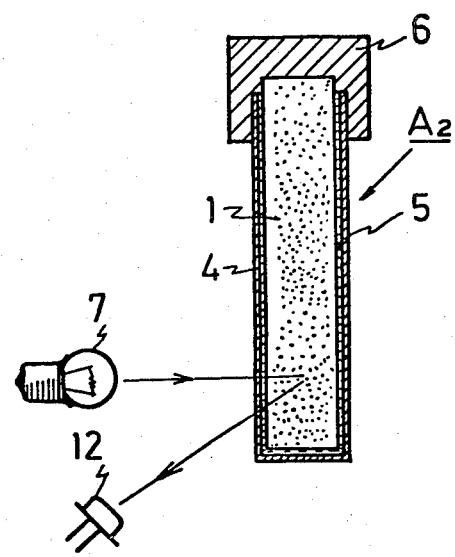

FIG. 6 shows the case where the light is made incident from the side face of a reference scatterer A2 which comprises a cylindrical transparent vessel 4 and a column shaped reference glass scatterer main body 1 having a plane base and a plane bottom, respectively. That is, the flux of light emitted from the light source lamp 7 impinges into the side face of the reference scatterer A2 passes through the transparent vessel 4, and enters into the silicone oil layer 5. In this case, the reference scatterer A2 has light consensing ability relative to the lateral direction of its own face having a curvature, but it has no condensing ability, because of the absence of the curvature, relative to the longitudinal direction of the column.

The flux of light, as mentioned above, advances through the layer of silicone 5 in such a manner as if through glass and reaches the reference glass scatterer main body. The scattered light dispersed by the microcrystals in the reference glass scatterer main body passes through the transparent vessel 4 by way of the silicone oil layer a second time and then is detected by means of the optical detector 12.

Figure 7:
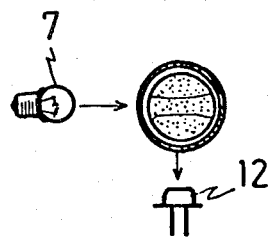
Figure 8:
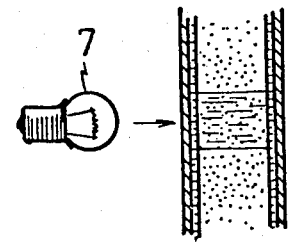

FIG. 7 is a typical diagram showing the flux of light within the reference scatterer A2 in FIG. 6, seen from above. FIG. 8 is a typical diagram showing the same, which is seen from the side.

In the embodiment of FIG. 6, a description was made of the case where the reference scatterer was of a column-shape. However, in the case where the side face of the scatterer is a plane surface, that is, for example, in the case of square pillar-shaped reference scatterer, the present invention can be used line in the former case. In this connection, as compared with the column-shaped reference glass scatterer A2, which has the condensing ability only relative to the lateral direction of its own face having a curvature, the square pillar-shaped reference scatterer has no condensing ability relatively to both lateral and longitudinal directions. Even so, this reference scatterer also can function satisfactorily as such.

As clearly understood from the above description, the reference scatterer according to the present invention is not subjected to any restriction in respect to the form and size of the transparent vessel and reference glass scatterer main body as its constituent elements. Whatever the shape, the scattered light output from the assembled reference scatterer can be obtained with long range stability. Accordingly the reference scatterer according to the present invention is applicable in whichever form it may be made.

Figure 9:
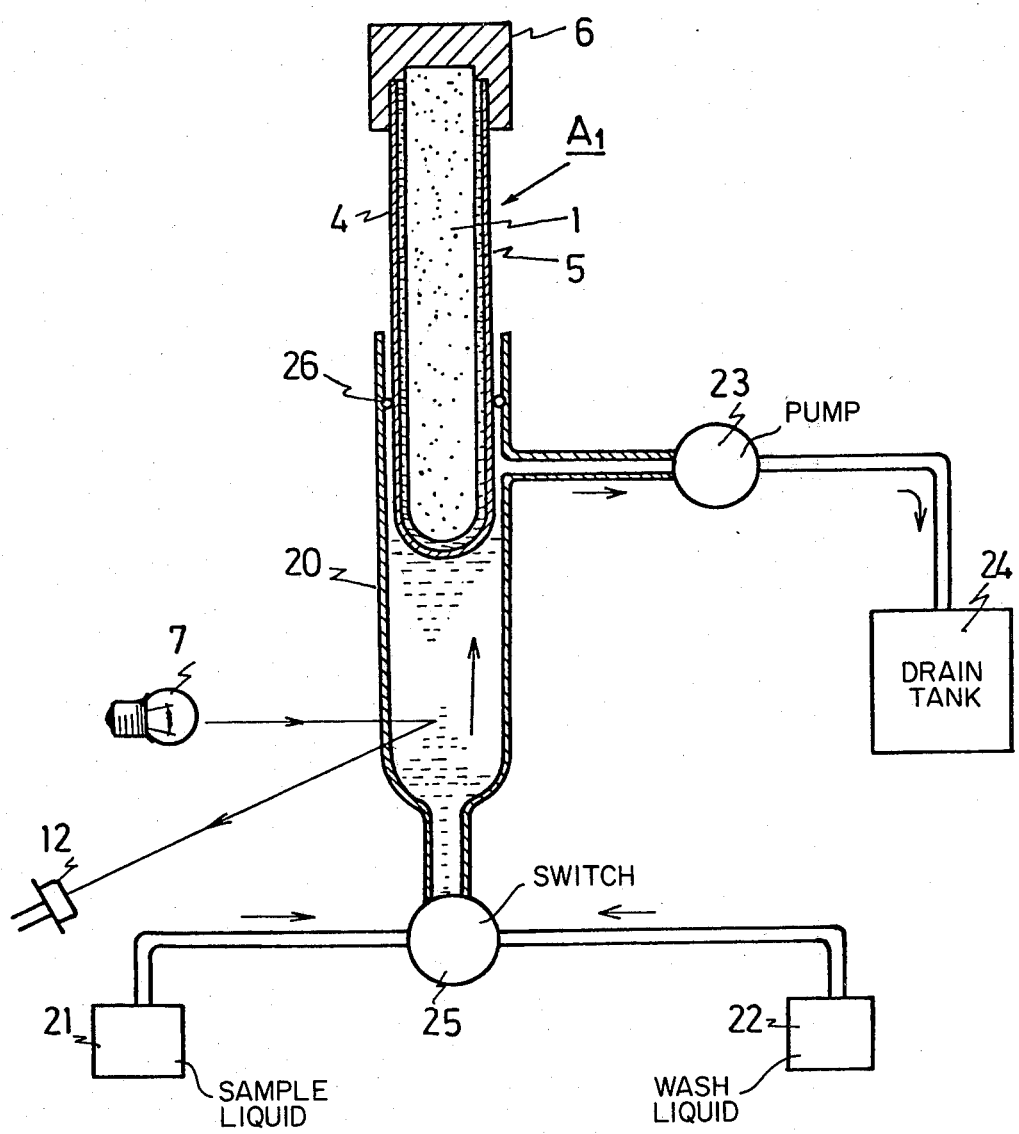

FIG. 9 shows still a further example, wherein the reference scatterer is incorporated into a flow cell 20 for the purpose of making the measurement automatic.

As seen in FIG. 9, the sample liquid 21 or the wash liquid 22 is drawn in by a suction sump 23, flows through the flow cell 20 in the direction of the arrow, and is discharged into a drain tank 24. The sample liquid 21 and the wash liquid 22 flow alternately into the flow cell 20 through a passage-change-over switch 25. The reference scatterer A1 is inserted into the vicinity of the top of the flow cell 20 with an "O-ring" 26 between the two, and moves up and down within the flow cell 20 manually or mechanically. In this case, the reference scatterer A1 also doubles as a plug for the flow cell 2.

At the time of measuring the sample liquid 21, the reference scatterer A1 is moved to the state "UP", and the light from the light source lamp 7 is made is irradiate into the flow cell 20. Then the scattered light dispersed from the sample liquid 21 enters into the optical detector 12 and an output $S_1$ is obtained. On completing the measurement of the sample liquid $21_1$, the reference scatterer A1 is moved to the state "DOWN", and the passage switch 25 is changed over so that the wash liquid 22 moves into the flow cell whereby the interior of the flow cell 20 is cleansed. After the cleansing is over, signals of the amount of scattered light emitted from the reference scatterer A1 is measured to obtain the output $R_1$. On completing the measurement of the reference scatterer A1, it is brought to the state "UP" a second time, and concurrently the passage change-over switch 25 is changed to the sample liquid $21_2$. The cycle described above is performed repeatedly.

The present invention relates to a reference scatterer for use in correction of scattering photometers, as described wherein the reference glass scatterer main body containing the microcrystals as a phase splitting of borosilicic acid in glass is accommodated within a transparent vessel, both forming a dual structure, and then the clearance between them is filled up with silicone oil or the like. Accordingly, it possesses a variety of characteristics which has never existed heretofore, as follows:

1. The surface of the reference scatterer is covered with a smooth face on which no microcrystals are formed, so that dirt or moisture is hard to adhere thereto. If dirt or moisture is adhered, it has no effect on the function of the reference scatterer as such.

2. The reference glass scatterer main body itself is covered directly with a chemically inactive liquid, so that it can maintain stability throughout the passage of time.

3. There is adopted in the capacity of the liquid for filling the clearance a liquid which has a refractive index approximately to that of glass, so that the reference glass scatterer main body may be used in case its surface finish is rough.

4. In the case where the transparent vessel as the outer tube is impaired with scratches or the like, it is possible to take out the reference glass scatterer main body therefrom and to reproduce thereby the reference scatterer as a whole without difficulty. 5. The reference scatterer according to the present invention is permitted to be made in whatever form and size.

What is claimed is:

1. A reference scatterer for use in the correction of scattering photometers comprising: a reference glass scatterer main body containing microcrystals for phase splitting incident light; a transparent vessel; a cap for said transparent vessel having means for coupling said reference glass scatter main body to said transparent vessel with a clearance between said body and said vessel; said body placed within said vessel with a clearance therebetween, and a liquid which fills the clearance and is prevented from leaking out of the transparent vessel by said cap.

2. A reference scatterer as in claim 1 wherein said liquid comprises silicone oil.

3. A reference scatterer as in either of claims 1 or 2 wherein said reference glass scatterer main body is formed in the shape of a column and said transparent vessel is tubular and of a complementary shape to the main body and having a closed bottom and an open top end, the inner diameter of said vessel being larger than the outer diameter of said reference glass scatterer main body.

4. A reference scatterer as in claim 3, wherein the bottom of said reference glass scatterer main body and the base of said transparent vessel are each formed with a respective curved surface to form a lens for incident light.

5. A reference scatterer as in claim 3, wherein the bottom of said reference glass main body and the base of said transparent vessel are each formed with a respective plane surface.

6. A reference scatterer as in claim 3 wherein the column shape of said reference glass scatterer main body is generally cylindrical.

7. A reference scatterer as in claim 6 where the bottom of said reference glass scatterer main body and the base of said vessel are each formed with respective curved surface to form a condensing lens for incident light.

8. A reference scatterer as in claim 2 wherein the column shape of said reference glass scatterer main body has at least one flat side.

9. A reference scatterer as in claim 8 where the bottom of said reference glass scatterer main body and the base of said vessel are each formed generally flat.

10. A reference scatterer as in claim 1 wherein microcrystals are of grown borosilicic acid.

11. A reference scatterer as in claim 3 wherein said reference glass scatterer main body has a portion which extends above the open end of said transparent vessel, said cap having a stepped recess having one part for fitting over said extending portion of said reference glass scatterer main body and a second part for engaging the outer surface of said transparent vessel adjacent said open end thereof to seal said vessel.

* * * * *